United States Patent
Lawrence et al.

(10) Patent No.: US 6,777,246 B2
(45) Date of Patent: Aug. 17, 2004

(54) TERTIARY AMINE COMPOUNDS FOR USE IN IMMUNOASSAYS

(75) Inventors: Christopher C. Lawrence, Fishers, IN (US); Armen B. Shanafelt, Carmel, IN (US)

(73) Assignee: Roche Diagnostics GmbH (DE)

( * ) Notice: Subject to any disclaimer, the term of this patent is extended or adjusted under 35 U.S.C. 154(b) by 318 days.

(21) Appl. No.: 10/025,378

(22) Filed: Dec. 18, 2001

(65) Prior Publication Data

US 2003/0138974 A1 Jul. 24, 2003

(51) Int. Cl.[7] .................. G01N 33/546; G01N 33/552; G01N 33/553; G01N 33/533
(52) U.S. Cl. .................. 436/533; 436/525; 436/527; 436/546; 436/825; 436/826
(58) Field of Search ................. 436/533, 525, 436/527, 825, 826, 546

(56) References Cited

U.S. PATENT DOCUMENTS

| | | |
|---|---|---|
| 4,292,038 A | 9/1981 | Kondo et al. |
| 4,362,531 A | 12/1982 | de Steenwinkel et al. |
| 4,536,478 A | 8/1985 | Sokoloff et al. |
| 5,486,479 A | 1/1996 | Ito et al. |
| 5,506,151 A | 4/1996 | Ito et al. |
| 5,643,732 A | 7/1997 | Strahilevitz |
| 5,846,751 A | 12/1998 | Pronovost et al. |
| 6,030,845 A | 2/2000 | Yamao et al. |
| 6,203,706 B1 | 3/2001 | Schwind et al. |
| 6,274,325 B1 | 8/2001 | Deger et al. |

FOREIGN PATENT DOCUMENTS

| | | |
|---|---|---|
| EP | 0 679 892 A1 | 11/1995 |
| WO | WO 97/06166 | 2/1997 |
| WO | WO 98/36277 | 8/1998 |
| WO | WO 02/03068 A1 | 1/2002 |

OTHER PUBLICATIONS

European Search Report from European Patent Application No. 02 02 4080, dated May 7, 2003, 4 pages.
J.L. Ortega–Vinuesa et al. *J. Biomater. Sci. Polymer Edn.*, 12(4), 379–408 (2001).
C.R. Martin et al. *Analytical Chemistry—News & Features*, May 1, 1998, 322A–327A.
R.G. Chapman et al. *J. Am. Chem. Soc.*, 122, 8303–8304 (2000).
N. Nakajima and Y. Ikada, *Bioconjugate Chem.*, 6, 123–130, (1995).
M. Yamaguchi et al. *J. Health Science*, 47(4), 419–423 (2001).
S. Perez–Amodio et al. *Anal. Chem.*, 73, 3417–3425 (2001).
P. Holownia et al. *Anal. Chem.*, 73, 3426–3421 (2001).
A. Singh et al. *J. Biosci.*, 25(1), 47–54 (2000).
J. Sackrison, "Covalent Coupling And Diagnostic Development Using Microspheres", 17 pages (1996).
Bangs Laboratories, Inc., Tech Note #13c—"Covalent Coupling Protocols", 9 pages.

*Primary Examiner*—Mary E. Ceperley
(74) *Attorney, Agent, or Firm*—Marilyn L. Amick; Roche Diagnostics Operations, Inc.

(57) ABSTRACT

A reagent for use in immunoassays reduces interference in particle agglutination assays. The reagent contains particles having covalently bound antibodies and a tertiary amine compound of formula (I):

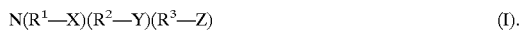

$$N(R^1{-}X)(R^2{-}Y)(R^3{-}Z) \qquad (I).$$

The moieties $R^1$, $R^2$, and $R^3$ are independently alkyl or alkyl ether. The moieties X, Y, and Z are independently —OH, —O—$R^4$, —S—$R^4$, —C(=O)—OH, —C(=O)—O$R^4$, or —C(=O)—NH$R^4$ ($R^4$ is alkyl).

18 Claims, 2 Drawing Sheets

*12.5 mM TEO*

*No TEO present*

TERTIARY AMINE COMPOUNDS FOR USE IN IMMUNOASSAYS

BACKGROUND OF THE INVENTION

In testing for analytes such as drug molecules, immunoassays have proven to be especially useful. In an immunoassay, the interaction of an analyte, sometimes referred to as an antigen, with a specific receptor, typically an antibody, results in the formation of an antigen-antibody complex. This complex can be detected by various measurements, such as radioactivity, fluorescence, light absorption and light scattering. The results are then correlated with the presence, absence, and ideally the concentration of the analyte.

One type of immunoassay is the particle-based agglutination immunoassay, which is based on the binding of an antigen with an antibody, one of which is bound to a particle. The particles employed are often polymer particles, such as polystyrene and poly(methyl methacrylate), which are typically produced by an emulsion polymerization process. Other particle systems may also be used, including gold particles such as gold nanoparticles and gold colloids; and ceramic particles, such as silica, glass, and metal oxide particles. The binding agent, which is an antigen or an antibody, may be physically adsorbed onto the particle; however, greater stability and longer shelf-life are obtained when the binding agent is covalently attached. See for example J. L. Ortega-Vinuesa et al. *J. Biomater. Sci. Polymer Edn.*, 12(4), 379–408 (2001).

Particles having covalently linked binding agents are typically prepared by activation of the particles, followed by coupling of the binding agent to the activated particles. In some instances, the activation is followed by a coupling of a linking group to the activated particles, and the linking group can then be used to tether the binding agent to the particle. Linking groups include, for example, avidin or streptavidin and chemical moieties presenting functional groups such as maleimides and thiols.

For particles having carboxylate groups bound to the surface, activation is often achieved by contacting the particles with a solution of a carbodiimide coupling reagent and a succinimide reagent such as N-hydroxysuccinimide (NHS) or N-hydroxysulfosuccinimide (sNHS). The carboxylate groups on the surface are thus converted into NHS-ester or sNHS-ester groups. Carbodiimide couplers include, for example, N-ethyl-N'-(3-dimethyl-aminopropyl) carbodiimide (EDC); dicyclohexylcarbodiimide (DCC); and diisopropylcarbodiimide (DIC). A binding agent or a linking group can then be coupled to the particles by mixing the activated particles and the binding agent or linking group in an aqueous mixture. Sensitized particles are formed once a binding agent has been linked to the surface, whether by contact with activated particles or by reaction with particles containing linking groups. An illustration of a simple version of this process, using NHS as the succinimide reagent and sensitizing with an antibody, is given in the following reaction scheme. The sensitized particles produced by this process are then typically treated with a blocking agent, for example bovine serum albumin (BSA), which serves to react with and quench remaining NHS or sNHS ester groups.

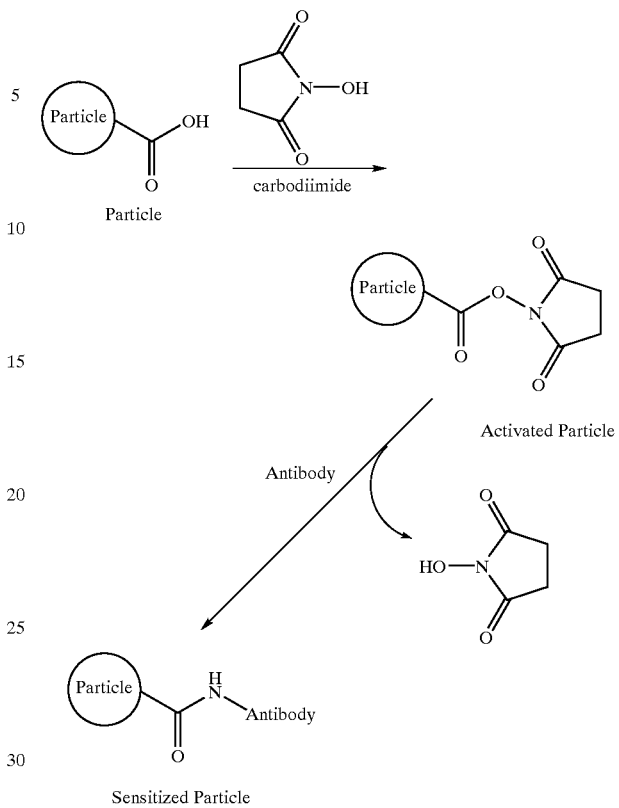

When such sensitized particles are mixed in an aqueous environment with a sample to be analyzed, the analyte in the sample will specifically bind to the antibody, which may be present on the particle or as a separate entity in the liquid mixture. This interaction may cause the particles to agglutinate (direct recognition), or it may hinder an agglutination process (competitive inhibition), depending on the particular format of the assay. Agglutination is the formation of clusters of particles having a larger collective size than that of an individual particle, and can be detected by measuring the change in the absorbance or the scattering of light by the sample. Ideally, the degree of agglutination in a particle-based agglutination immunoassay can be correlated with the amount of antigen in the sample. However, non-specific interactions between the particles and the sample can result in agglutination or inhibition of agglutination of the particles which is unrelated to the antigen-antibody interaction. These unwanted interactions can cause false positive or false negative results, and can also lead to inaccurate correlations of the agglutination response to the concentration of the antigen of interest. All of these undesirable effects compromise the quality of the assay result, and are collectively known as "interference."

Various substances have been reported to reduce interference in agglutination immunoassays by suppressing non-specific interactions. For example, U.S. Pat. No. 4,362,531 describes the use of salts such as guanidinium salts, thiocyanate salts, and alkali metal halide salts. In addition, U.S. Pat. Nos. 5,506,151 and 5,486,479 describe the use of primary, secondary, and tertiary amines such as 1-ethyl-3-(3-dimethylaminopropyl)urea (EDU), 3-dimethylaminopropylamine, 3-diethylaminopropylamine, dimethylaminopropylchloride, and 1-cyclohexyl-3-(2-morpholinoethyl) carbodiimide metho-p-toluenesulfonate (CMC). Other substances reported include halogen substituted carboxylic acids (U.S. Pat. No. 4,536,478) and substituted amides (U.S. Pat. No. 4,292,038). In general, these additives do not provide an optimum balance between reducing the interference due to non-specific interactions and minimizing the reactivity of the additive towards the antibody or antigen of interest. Non-specific interactions between the additive and the antibody or antigen can also contribute to interference in the immunoassay.

It is thus desirable, in particle-based agglutination immunoassays, to prevent non-specific interactions between the particles and components of the sample being analyzed. It is also desirable to provide additives which can suppress non-specific interactions within the immunoassay while avoiding interactions with the antigen or antibody.

SUMMARY OF THE INVENTION

In one aspect of the invention there is a reagent for use in immunoassays, comprising a plurality of particles and a tertiary amine compound of formula (I)

wherein $R^1$, $R^2$, and $R^3$ are independently selected from the group consisting of alkyl and alkyl ether; and X, Y, and Z are independently selected from the group consisting of —OH, —O—$R^4$, —S—$R^4$, —C(=O)—OH, —C(=O)—O$R^4$, or —C(=O)—NH$R^4$, wherein $R^4$ is alkyl. Each of said particles comprises a surface having been activated by a carbodiimide, and a binding agent linked to the surface through a covalent bond.

In another aspect of the invention, there is a reagent for use in immunoassays, comprising a plurality of particles and a tertiary amine compound of formula (II)

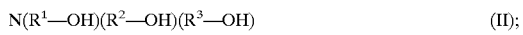

wherein $R^1$, $R^2$, and $R^3$ are independently alkyl groups comprising from 1 to 5 carbon atoms; wherein the reagent forms an assay mixture when mixed with a sample, such that the tertiary amine compound is present in the assay mixture in a concentration of 50 mM or less. Each of said particles comprises a surface having been activated by a carbodiimide, and a binding agent linked to the surface through a covalent bond.

In yet another aspect of the invention there is an assay method for determining an analyte, comprising combining a sample suspected of containing said analyte with any of the above reagents, and determining the presence or amount of said detectable complex as a measure of said analyte in said sample. The reagent comprises the antibody of said analyte, and the reagent is capable of forming a detectable complex with said analyte.

In yet another aspect of the invention there is provided a test kit, comprising any of the above reagents.

In yet another aspect of the invention there is provided, in an immunoassay method wherein a sample suspected of containing an analyte is combined with a plurality of particles, each of said particles having a surface having been activated by a carbodiimide, and a binding agent bound to the surface through a covalent bond; the improvement comprising adding to the sample, to form an assay mixture, a tertiary amine compound of formula (I)

wherein $R^1$, $R^2$, and $R^3$ are independently selected from the group consisting of alkyl and alkyl ether; and X, Y, and Z are independently selected from the group consisting of —OH, —O—$R^4$, —S—$R^4$, —C(=O)—OH, —C(=O)—O$R^4$, or —C(=O)—NH$R^4$, wherein $R^4$ is alkyl.

DETAILED DESCRIPTION

Figure 1:
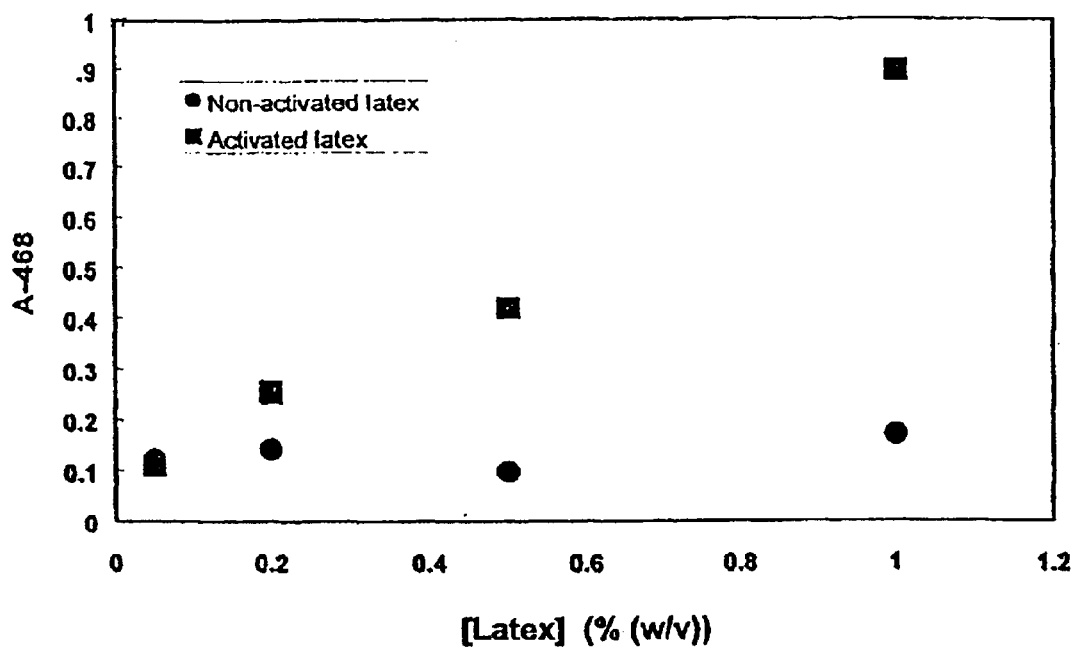
FIG. 1 is a graph of the dependence of the absorbance at 468 nm due to bound acid orange 7 dye as a function of particle concentration.

The present invention is intended to reduce interference in particle agglutination immunoassays. Particles which have been activated with a carbodiimide and either NHS or sNHS and then sensitized with a binding agent are used in immunoassays in the presence of certain tertiary amine compounds. The tertiary amine compounds used in the present invention are remarkably effective in the prevention of non-specific interactions between the particles and sample components. The reduction or elimination of non-specific interactions improves the accuracy of the immunoassay.

Particle agglutination immunoassays of an analyte utilize particles which contain a binding agent on their surface. The antibody of the analyte undergoes a specific interaction with an analyte in the sample to be analyzed and optionally with a conjugate of the analyte also present in the assay mixture. These interactions affect the degree of aggregation of the particles, and this aggregation can be monitored and correlated with the amount of the analyte in the sample. The agglutination immunoassays may be direct assays, in which the binding of the antibody and analyte directly affect the aggregation; or they may be competitive inhibition assays, in which the analyte competes with a conjugate derivative of the analyte for binding with the available antibody.

Analyte refers to the substance, or group of substances, whose presence or amount thereof in a liquid medium is to be determined including, but not limited to, any drug or drug derivative, hormone, protein antigen, oligonucleotide, hapten, or hapten-carrier complex. An analyte analog is any substance, or group of substances, which behaves in a similar manner to the analyte, or in a manner conducive to achieving a desired assay result with respect to binding affinity and/or specificity of the antibody for the analyte including, but not limited to, derivatives, metabolites, and isomers thereof.

Antibody means a specific binding partner of the analyte and is meant to include any substance, or group of substances, which has a specific binding affinity for the analyte to the exclusion of other substances. The term includes polyclonal antibodies, monoclonal antibodies and antibody fragments.

A peptide is any compound formed by the linkage of two or more amino acids by amide (peptide) bonds, usually a polymer of α-amino acids in which the α-amino group of each amino acid residue (except the $NH_2$-terminal) is linked to the α-carboxyl group of the next residue in a linear chain.

The terms peptide, polypeptide and poly(amino acid) are used synonymously herein to refer to this class of compounds without restriction as to size. The largest members of this class are referred to as proteins.

A covalent bond is a chemical bond between two species, and may involve single bonds or multiple bonds. The term "covalent" does not include hydrophobic/hydrophilic interactions, Hydrogen-bonding, van der Waals interactions, and ionic interactions.

Any sample that is suspected of containing the analyte can be analyzed by the method of the present invention. The sample is typically an aqueous solution such as a body fluid from a host, for example, urine, whole blood, plasma, serum, saliva, semen, stool, sputum, cerebral spinal fluid, tears, mucus or the like, but preferably is urine, plasma or serum. The sample can be pretreated if desired and can be prepared in any convenient medium. An aqueous medium is preferred.

Calibration material means any standard or reference material containing a known amount of the analyte to be measured. The sample suspected of containing the analyte and the calibration material are assayed under similar conditions. Analyte concentration is then calculated by comparing the results obtained for the unknown specimen with results obtained for the standard.

Particles which may be used in agglutination immunoassays include any type of particle which are activated using carbodiimide chemistry. Such particles include, for example, polymer particles including polystyrene and poly(methylmethacrylate); gold particles including gold nanoparticles and gold colloids; and ceramic particles including silica, glass, and metal oxide particles. See for example C. R. Martin et al. *Analytical Chemistry—News & Features*, May 1, 1998, 322A–327A.

These particles may be activated using carbodiimide chemistry directly, or they may be activated once their surfaces have been modified to contain carboxylate groups. Carboxylate groups can be introduced to surfaces, for example by hydrolysis reactions, by treatment with a carboxylating reagent, or by formation of self-assembled monolayers (SAMs) containing carboxylate groups. See for example R. G. Chapman et al. *J. Am. Chem. Soc.,* 122, 8303–8304 (2000). Activated particles are then mixed with an antibody, optionally followed by exposure to BSA, to produce sensitized particles. These sensitized particles may be further treated with a primary amine compound to prevent covalent interactions between sample components and any residual NHS or sNHS esters on the particle surface. Suitable primary amines include, for example, glycine ethyl ester, 2-(aminoethoxy)ethanol (AEO); 2,2'-(ethylenedioxy) bisethylamine (EBE); or 4,7,10-trioxa-1,3-tridecanediamine (TTD) as described in co-pending application Ser. No. 10/025,196, entitled "Particles For Immunoassays And Methods For Treating The Same" filed Dec. 18, 2001, with inventors C. C. Lawrence et al., the disclosure of which is incorporated herein by reference.

Analysis of the carbodiimide activation chemistry reveals that tertiary amine functional groups linked to the surface of the particles can be formed by conversion of the intermediate O-acylisourea intermediate to an N-acylurea moiety. During the conversion of the particle-bound carboxylate groups into NHS-esters or sNHS-esters, it is believed that the presence of excess EDC can lead to the formation of N-acylurea moieties on the particle surface as illustrated in the following reaction scheme. These N-acylurea moieties are likely stable during the subsequent processing steps (sensitization and treatment with primary amine) and under normal immunoassay conditions.

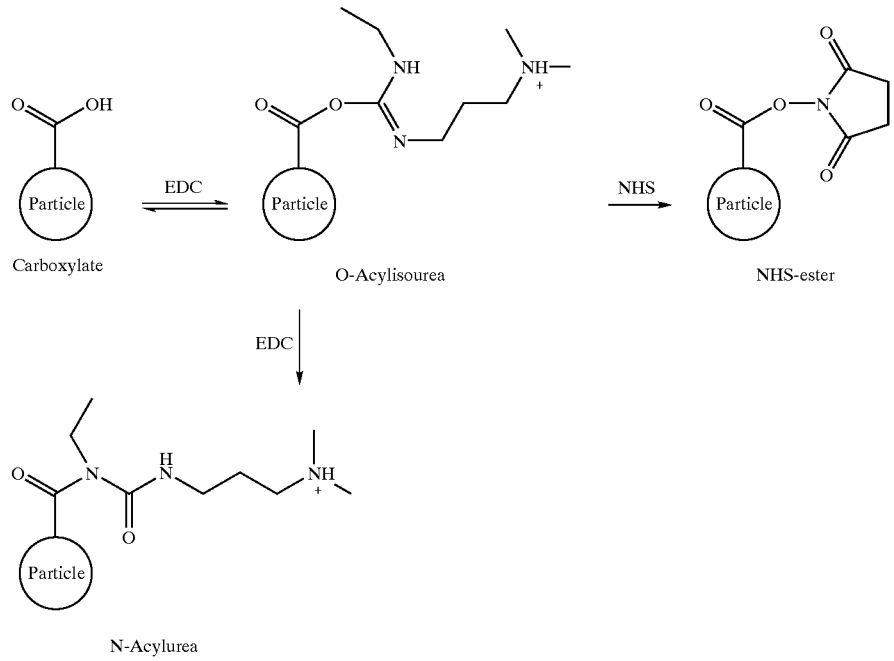

The conversion of the O-acylisourea group to the N-acylurea group competes both with the desired esterification between the O-acylisourea intermediate and NHS or sNHS and with the hydrolysis of the intermediate back to the free carboxylate. The hydrolysis reaction of the O-acylisourea to the carboxylate is believed to predominate over both the esterification reaction and the N-acylurea forming side reaction. The formation of the N-acylurea moiety may be catalyzed by a second equivalent of the carbodiimide (N. Nakajima and Y. Ikada, Bioconjugate Chem., 6, 123–130, (1995)). Typical activation protocols call for NHS to be added to the particle suspension before EDC is added to initiate the reactions. Once the O-acylisourea intermediate is formed, its rate of conversion to an N-acylurea moiety is minimized under these conditions. The rate of this side-reaction is more problematic when a high degree of carboxylate activation is desired, since this requires the use of a large number of equivalents of EDC.

The presence of N-acylurea moieties on the particle surface is undesirable. This group and its linkage to the particle are chemically stable, and thus can remain on the microparticle throughout all of the subsequent preparatory steps, including both the sensitization with binding agent and bovine serum albumin, as well as the quenching of any residual NHS-esters or sNHS-esters with a primary amine. Moreover, the tertiary amine group at the terminus of the N-acylurea moiety will be protonated under the pH conditions of the immunoassay (5<pH<9) and therefore has the potential to engage in non-specific electrostatic interactions with appropriately charged or polar components present in the sample being analyzed.

The effects of the N-acylurea groups on the accuracy of an immunoassay can be observed by analyzing the interaction of immunoassay particles with a dye which, like many proteins, can interact with the tertiary amine of the N-acylurea group. Referring to FIG. 1, particles which have been activated and treated with a primary amine adsorb the dye on their surface, as measured by the optical absorbance of the particles. The dye in this case is acid orange 7, which is a dye with affinity for amino groups which have been protonated under acidic pH conditions. The dye binds to particles which have been subjected to a carbodiimide activation step, and this binding is dependent on the concentration of particles in the dye—particle mixture. In contrast, significant binding of the dye does not occur with particles which have not been subjected to the activation procedure. The binding of the dye is a model for the non-specific interactions that can occur between particles and sample components, resulting in interference.

The interference generated by the presence of N-acylurea groups on the particle surface can be reduced or eliminated by the presence of a tertiary amine compound of formula (I) in the immunoassay mixture:

$$N(R^1—X)(R^2—Y)(R^3—Z) \qquad (I),$$

where $R^1$, $R^2$, and $R^3$ are independently alkyl or alkyl ether; and X, Y, and Z are independently —OH, —O—$R^4$, —S—$R^4$, —C(=O)—OH, —C(=O)—O$R^4$, or —C(=O)—NH$R^4$, where $R^4$ is alkyl. "Alkyl" refers to a substituted or unsubstituted, straight, branched or cyclic hydrocarbon chain. "Alkyl ether" refers to an alkyl group containing at least one —C—O—C-bond. Preferably, $R^1$, $R^2$, $R^3$, and $R^4$ are independently alkyl groups containing from 1 to 5 carbon atoms. More preferably, $R^1$, $R^2$, $R^3$, and $R^4$ independently contain from 1 to 3 carbon atoms. Preferably, X, Y, and Z are independently —OH or —O—$R^4$. More preferably, X, Y, and Z are all —OH.

Without wishing to be bound by any theory of operation, it is believed that the tertiary amine compounds reduce interference by interacting electro-statically and non-specifically with sample components which would otherwise engage in non-specific electrostatic interactions with the tertiary amine functionality of the N-acylurea moieties present on the particle surface. The tertiary amine compounds effectively function as decoys, thus minimizing or eliminating the interactions between N-acylureas and sample components. The inhibition of non-specific interactions involving the particles improves the accuracy of the immunoassay.

The tertiary amine compounds may be combined in an aqueous mixture with the particles, or they may be combined with the sample before the sample is mixed with the particles. The "reagent" added to the sample to perform the immunoassay thus can be a single component containing particles and the tertiary amine compound; or it can be more than one component, where each component can be added to the sample alone or in combination. It is preferred that, in the final mixture which is analyzed, referred to as the assay mixture, the tertiary amine compound is present in a concentration of 50 mM or less. More preferably, the tertiary amine compound is present in a concentration of 25 mM or less. Even more preferably, the tertiary amine compound is present in a concentration of 12.5 mM or less. Even more preferably, the tertiary amine compound is present in a concentration of 5 mM or less.

It is preferred that —$R^1$—X, —$R^2$—Y, and —$R^3$—Z are independently electron-withdrawing groups. An electron-withdrawing group contains an element or group of elements at or near its terminus which is more electronegative than the element to which the electron-withdrawing group is attached. In these examples, the electronegative portion is identified as X, Y, and Z. The effect of an electron-withdrawing group is to increase the partial positive charge on the central tertiary nitrogen by attracting electron density toward the X, Y, and Z groups and away from the central nitrogen. A tertiary nitrogen with increased partial positive charge has an increased ability to interact electrostatically with substances which are charged or polar. The —$R^1$—X, —$R^2$—Y, and —$R^3$—Z groups of the tertiary amine compounds of the present invention are not the strongest electron-withdrawing moieties known. However, these groups represent a balance of electronegativity and chemical stability. Other electron-withdrawing groups would likely be reactive towards sample components including the antibody or antigen of interest.

Figure 4:
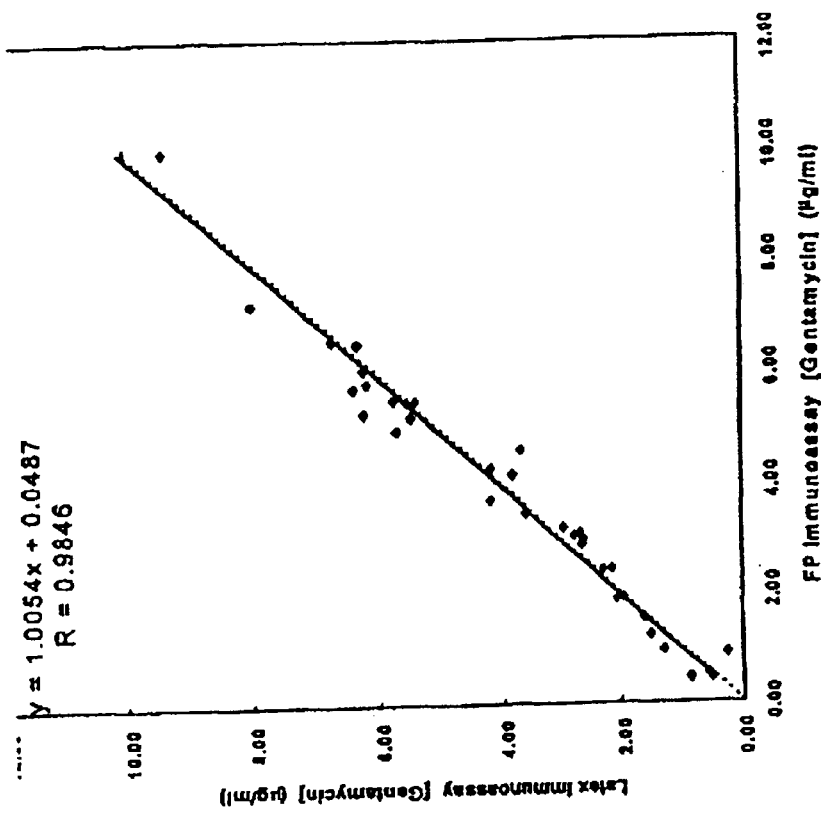
FIG. 4 is a graph correlating the measurements of gentamicin immunoassays performed by fluorescence polarization and by particle agglutination with TEO present.
Figure 3:
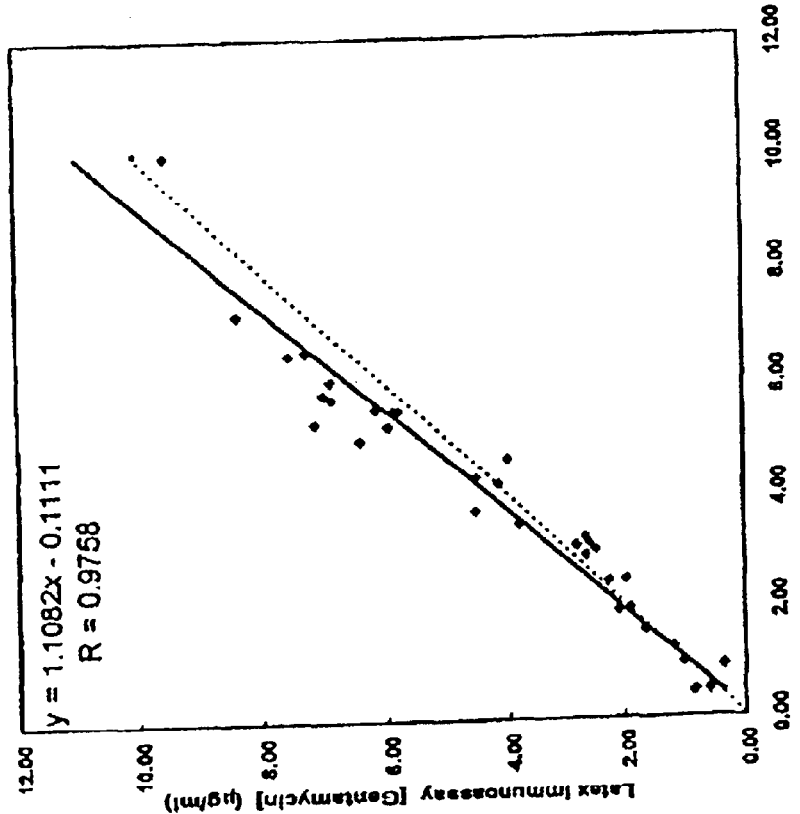
FIG. 3 is a graph correlating the measurements of gentamicin immunoassays performed by fluorescence polarization and by particle agglutination without triethanolamine (TEO) present.

Although the tertiary amine compounds of the present invention compete with particle-bound N-acylureas for non-specific interaction with sample components, they do not interfere with the specific interaction of the particle-bound antibody with the antigen of interest. In fact, the performance of immunoassays utilizing the tertiary amine compounds is improved by the lack of interference. FIGS. 3 and 4 together illustrate the improved performance of particles of the present invention in an immunoassay. FIG. 3 is a graph correlating the measurements of an immunoassay for gentamicin performed by fluorescence polarization (FP) with the measurements of an immunoassay for gentamicin performed by particle agglutination with no added tertiary amine compound. FIG. 4 is a graph correlating the same FP gentamicin measurements with gentamicin measurements from a particle agglutination immunoassay using a tertiary amine compound additive, in this case 12.5 mM triethanolamine (N(CH$_2$CH$_2$OH)$_3$; TEO). The best-fit line correlating the data points should ideally be linear with a slope of 1, a y-axis intercept of zero, and a correlation coefficient (R) of 1. By each of these three measures the performance of the assay containing TEO is superior to that performed without TEO. The presence of the tertiary amine compound provides a slope of the best-fit line of 1.01, whereas its absence provides a slope of the best-fit line of 1.11. The presence of the tertiary amine compound provides an intercept of 0.05, whereas the absence provides an intercept of −0.11. The tertiary amine compound provides an R value of 0.985, whereas the absence of tertiary amine compound provides an R value of 0.976. These comparative results also are visually apparent by comparison of the ideal line with the best-fit line calculated from the data.

A comparison of tertiary amines as additives to particle agglutination immunoassays reveals that the tertiary amine compounds of the present invention provide for more accurate results than do other tertiary amines. Referring to Example 3 and Table A herein, which compare the parameters of best fit lines for a variety of tertiary amines in a gentamicin immunoassay, the best fit line for TEO has the most favorable combination of values, not only for the slope, but also for the intercept and the R value. Although other tertiary amines have one or two favorable values for the best fit parameters, TEO has favorable values for all three. For example, triethylamine has intercept and R values similar to those of TEO; however triethylamine has a slope value farther from 1.0 than does TEO.

These results demonstrate that an improved performance of a particle based immunoassay can be obtained by including a tertiary amine compound of the present invention in the assay mixture. The inclusion of a tertiary amine compound may be used alone or in combination with other techniques for reducing interference in an immunoassay. In optimizing the performance of particle agglutination immunoassays, it may be preferred to include a tertiary amine compound of the present invention in the assay mixture, and also to use sensitized particles which have been treated with a primary amine compound, as described in the above mentioned co-pending application Ser. No. 10/025,196, entitled "Particles For Immunoassays And Methods For Treating The Same" filed Dec. 18, 2001, with inventors C. C. Lawrence et al. In some cases, the use of sensitized particles treated with a primary amine, such as glycine ethyl ester, AEO, EBE and TTD, may be sufficient to reduce the interference of the immunoassay to the desired level. The use of either the primary amine particle treatment or the tertiary amine compound additive, alone or in combination, can be determined empirically to determine if one technique is better than the other or if the combination yields the best results.

Without wishing to be bound by any theory, it is believed that failure to compete with the N-acylurea group in this fashion can instead result in the interaction of the N-acylurea with protein components of the biological fluid during the immunoassay. This in turn interferes with the kinetics and/or thermodynamics of the particle agglutination process, both in the case of biological fluid samples which contain the target analyte and those samples which do not, leading in both instances to erroneous assay results.

Various ancillary ingredients will frequently be employed in an assay in accordance with the present invention. For example, buffers will normally be present in the assay medium, as well as stabilizers for the assay medium and the assay components. Frequently, in addition to these additives, additional proteins may be included, such as albumin; or surfactants may be included, particularly non-ionic surfactants and the like.

The tertiary amine compound may, along with other components of the immunoassay system, be packaged in a kit useful for conveniently performing the assay methods for the determination of an analyte. To enhance the versatility of the subject invention, components can be provided in packaged combination, in the same or separate containers, in liquid or lyophilized form so that the ratio of the components provides for substantial optimization of the method and assay. The components may each be in separate containers, or various components can be combined in one or more containers depending on the cross-reactivity and stability of the components. Preferably, the sensitized particles containing the binding agent and the tertiary amine are in the same container, such that they are added to the sample as a single liquid mixture.

For example, a test kit may contain, in packaged combination, a tertiary amine compound, an antibody specific for a particular analyte, a sensitized particle containing the antibody or a derivative of the analyte, an analog or derivative of the antibody, or a conjugated derivative of the analyte. Specific kit combinations include a first package containing the tertiary amine and the antibody together with a second package containing the particle containing the analyte derivative; a first package containing the tertiary amine and the particle containing the antibody together with a second package containing the conjugated analyte derivative; and a single package containing the tertiary amine, the particle containing the antibody, and the conjugated analyte derivative. The kit may also comprise one or more calibrators comprising a known amount of the analyte. Such a test kit may provide reagents for an assay with enhanced clinical sensitivity for the analyte and structurally related compounds.

EXAMPLES

The following examples are provided by way of illustration and should not be seen as limiting the scope of the present invention.

Latex particles having an average diameter of 201 nanometers (nm), a surface area of 28.4 square meters per gram ($m^2/g$), and containing 0.21 milliequivalents (meq) surface carboxylate groups per gram of latex were obtained from SERADYN (Indianapolis) and used without further characterization. Microparticle agglutination immunoassays were performed on a HITACHI 717 analyzer (ROCHE DIAGNOSTICS CORPORATION, Indianapolis) and their performance assessed with reference to results from ROCHE fluorescence polarization (FP) immunoassays which were conducted in parallel on an INTEGRA 700 analyzer (ROCHE DIAGNOSTICS SYSTEMS). ROCHE FP calibrators were used to construct a calibration curve for the microparticle-based assay. Resuspension of latex pellets was effected using a ULTRASONIC HOMEGENIZER-4710 SERIES sonicator (COLE-PARMER, Vernon Hills, Ill.) at 25–50% output power while maintaining the sample on ice and latex monodispersity was assessed on a COBAS MIRA analyzer (ROCHE DIAGNOSTICS SYSTEMS) by light absorption at multiple wavelengths.

Solvents and buffers were obtained from FISHER SCIENTIFIC (Suwanee, Ga.). All other reagents were obtained from ALDRICH (Milwaukee, Wis.) or from FLUKA and were used as received.

Example 1

Formation of N-acylurea Groups During Carbodiimide Activation

To a suspension of 50 ml of 1% (w/v) latex in 10 mM 2-morpholinoethanesulfonic acid (MES) having a pH of 5.0, was added 4.78 ml a freshly prepared aqueous solution of 0.22 M NHS, followed by 4.03 ml of a freshly prepared aqueous solution of 0.26 M 1-ethyl-3-(3-dimethylaminopropyl) carbodiimide (EDC). After incubation at room temperature for 2 hr, the suspension was centrifuged (15,000×g, 30 min), and the latex resuspended in 25 ml of 50 mM 3-morpholinopropanesulfonic acid (MOPS) having a pH of 8.0. To this suspension was added 25 ml of 0.84M 2-(aminoethoxy)ethanol (AEO) in 50 mM MOPS at pH 8.0. After incubation at room temperature for 2 hr, the latex was centrifuged (15,000×g, 30 min), resuspended in 50 ml of 50 mM MOPS at pH 7.0, and centrifuged again. This process was repeated three more times. The final latex pellets were resuspended in 50 mM MES at pH 5.0 and stored as 2% (w/v) suspensions at 4° C.

Incubations were performed on 1 ml samples containing 0.05–1.0% (w/v) of the latex prepared above and 2 mM acid orange 7 dye, which was added as a 50 mM aqueous stock solution. The pH of the sample was adjusted to 3.0 with 1 M HCl, and the samples were incubated at room temperature overnight. Control incubations were performed using latex which had not been subjected to the activation procedure with EDC and NHS. The latex was collected by centrifugation (15,000×g, 30 min), resuspended in 1 ml H$_2$O (pH 3.0), and centrifuged again to remove unbound dye. This procedure was repeated five more times. The resulting pellet was resuspended in 1 ml of 30% (v/v) ethanolamine in water and centrifuged once more. The absorbance of the supernatant liquid at 468 nm was then measured.

Figure 2:
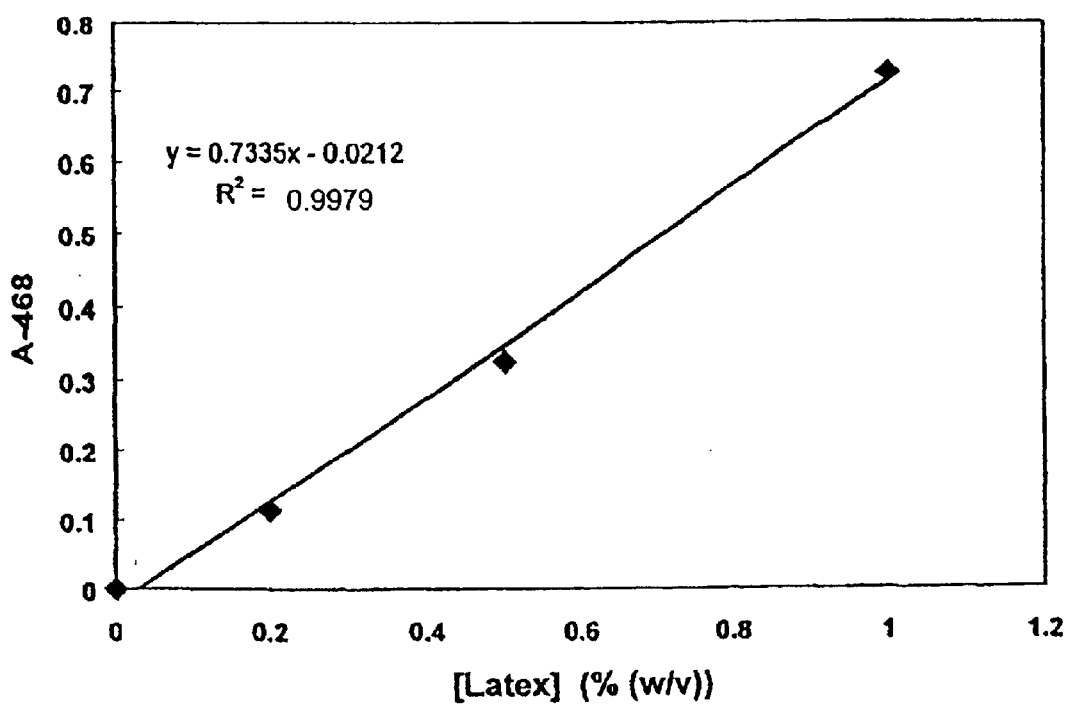
FIG. 2 is a graph of the dependence of the absorbance at 468 nm due to bound acid orange 7 dye as a function of particle concentration, with background signal subtracted.

The dependence of the absorption at 468 nm as a function of particle concentration is shown in the graphs of FIG. 1. The binding of acid orange 7 to the non-activated latex particles was taken as the background binding, and subtraction of these values from the binding observed with the activated-quenched latex at each latex concentration yields the data shown in FIG. 2. From the slope of the best-fit line ($R^2$=0.998) and the extinction coefficient of the dye, which had been determined as $\epsilon_{468}$=13,200 M$^{-1}$ cm$^{-1}$, on average one in every 38 of the carboxylate residues on the latex surface was converted to an N-acylurea moiety during the activation—esterification procedure. This calculation assumes a 1:1 stoichiometry of interaction between an N-acylurea moiety and an acid orange 7 molecule. Such an assay can thus be used to monitor and optimize activation conditions of carboxylic acid groups by carbodiimides.

Example 2

Use of Triethanolamine as an Additive to Improve Immunoassay Performance

Latex agglutination immunoassays were performed using latex particles which had been sensitized with a gentamicin monoclonal antibody and treated with AEO. Immunoassays were performed in the absence of triethanolamine (TEO) and in the presence of TEO at final concentrations in the range of 2.5–15 mM. The gentamicin content of each serum sample tested was determined by the commercially available Roche FP gentamicin immunoassay which uses the same gentamicin monoclonal antibody as the latex-based assay. The FP reference immunoassays and the latex agglutination immunoassays were performed in parallel to avoid sample degradation. The inclusion of TEO in the latex immunoassay buffer did not significantly affect the quality of the calibration curve obtained.

FIGS. 3 and 4 show correlation graphs of the microparticle-based immunoassays either in the absence of TEO or in the presence of 12.5 mM TEO, with the Roche FP immunoassay. Inclusion of TEO as an additive has a dramatic effect on the performance of the latex agglutination immunoassay. Relative to the control experiment (no TEO), the slope of the best-fit line decreases from 1.11 to 1.01, the y-axis intercept changes from −0.11 to 0.05 and the R correlation coefficient increases from 0.976 to 0.985. Thus the three parameters move closer to the optimal values of 1.00, 0.00 and 1.000 respectively, as is visually apparent from the merging of the best-fit line (solid line) to the target line (dotted line (slope=1, intercept=0)). A similar beneficial effect of including TEO in the microparticle based assay formulation was seen when the latex was tested with a set of serum samples which had tested negative for gentamicin by the Roche FP immunoassay. When the final assay mixture contained 12.5 mM TEO, the mean apparent gentamicin concentration in this sample set was −0.32 µg/ml compared to 0.42 µg/ml in the absence of TEO. The desired lower limit of detection of this assay is 0.17 µg/ml. Optimization studies suggested that a final TEO concentration of 5 mM was sufficient for the benefits afforded by this additive to be fully realized.

Example 3

Comparative Results of Immunoassays Using Tertiary Amines

Latex agglutination immunoassays for gentamicin were performed as in Example 2, but using a variety of tertiary amines. For each immunoassay, 12.5 mM of a tertiary amine was present. The tertiary amines examined were TEO and the following compounds, previously described in U.S. Pat. Nos. 5,506,151 and 5,486,479:

1-ethyl-3-(3-dimethylaminopropyl)urea (EDU),
3-dimethylaminopropylamine,
3-diethylaminopropylamine,
dimethylaminopropylchloride, and triethylamine.

The parameters of the best fit lines for each set of data are given in Table A. The tertiary amine having the slope closest to one was TEO. The tertiary amines having an intercept closest to zero were EDU, triethylamine and TEO. The tertiary amines having an R value closest to one were dimethylaminopropylchloride and TEO.

TABLE A

| Tertiary Amine | Slope | Intercept | R |
|---|---|---|---|
| Control | 1.108 | −0.111 | 0.976 |
| EDU | 1.094 | −0.046 | 0.980 |
| 3-dimethylamino-propylamine | 1.098 | −0.211 | 0.986 |
| 3-diethylamino-propylamine | 1.040 | −0.099 | 0.983 |
| dimethylamino-propylchloride | 1.030 | −0.178 | 0.985 |
| triethylamine | 1.031 | 0.040 | 0.983 |
| triethanolamine (TEO) | 1.005 | 0.049 | 0.985 |

What is claimed is:

1. A reagent for use in immunoassays, comprising:
a plurality of particles, each of said particles comprising a surface having been activated by a carbodiimide;
a binding agent selected from the group consisting of antigens and antibodies linked to the carbodiimide through a covalent bond; and
a tertiary amine compound of the formula N(R$^1$—X)(R$^2$—Y)(R$^3$—Z) wherein R$^1$, R$^2$, and R$^3$ are independently selected from the group consisting of alkyl and alkyl ether; and X, Y, and Z are independently selected from the group consisting of —OH, —O—R$^4$, —S—$R^4$, —C(=O)—OH, —C(=O)—$OR^4$, and —C(=O)-$NHR^4$, wherein $R^4$ is alkyl.

2. The reagent of claim 1, wherein $R^1$, $R^2$, $R^3$ and $R^4$ are independently alkyl groups comprising from 1 to 5 carbon atoms.

3. The reagent of claim 1, wherein X, Y, and Z are independently selected from the group consisting of —OH and —O—$R^4$.

4. The reagent of claim 1, wherein $R^1$, $R^2$, and $R^3$ are independently alkyl groups comprising from 1 to 5 carbon atoms; and X, Y, and Z are —OH.

5. The reagent of claim 1, wherein the tertiary amine compound is triethanolamine.

6. The reagent of claim 1, wherein the particles further comprise the reaction product of a succinimide ester and a primary amine compound on the surface.

7. The reagent of claim 6, wherein the primary amine compound is selected from the group consisting of glycine ethyl ester; 2-(aminoethoxy)ethanol; 2,2'-(ethylenedioxy)bisethylamine; and 4,7,10-trioxa-1,3-tridecanediamine.

8. The reagent of claim 1, wherein the plurality of particles and the tertiary amine compound are present in a single liquid mixture.

9. A reagent for use in immunoassays, comprising:
   a plurality of particles, each of said particles comprising a surface having been activated by a carbodiimide;
   a binding agent selected from the group consisting of antigens and antibodies linked to the carbodiimide through a covalent bond; and
   a tertiary amine compound of the formula N($R^1$—OH)($R^2$—OH)($R^3$—OH) wherein $R^1$, $R^2$, and $R^3$ are independently alkyl groups comprising from 1 to 5 carbon atoms; wherein the reagent forms an assay mixture when mixed with a sample, such that the tertiary amine compound is present in the assay mixture in a concentration of 50 mM or less.

10. The reagent of claim 9, wherein the tertiary amine compound is triethanolamine.

11. The reagent of claim 9, wherein the particles further comprise the reaction product of a succinimide ester and a primary amine compound on the surface; wherein the primary amine is selected from the group consisting of glycine ethyl ester; 2-(aminoethoxy)ethanol; 2,2'-(ethylenedioxy)bisethylamine; and 4,7,10-trioxa-1,3-tridecanediamine.

12. The reagent of claim 9, wherein the plurality of particles and the tertiary amine compound are present in a single liquid mixture.

13. An assay method for determining an analyte, comprising:
   combining a sample suspected of containing said analyte with the reagent of claim 1, wherein the binding agent is specific for the analyte and forms a detectable complex with said analyte; and
   determining the presence or amount of said detectable complex as a measure of said analyte in said sample.

14. An assay method for determining an analyte, comprising:
   combining a sample suspected of containing said analyte with the reagent of claim 4, wherein the binding agent is specific for the analyte and forms a detectable complex with said analyte; and
   determining the presence or amount of said detectable complex as a measure of said analyte in said sample.

15. An assay method for determining an analyte, comprising:
   combining a sample suspected of containing said analyte with the reagent of claim 13, wherein the binding agent is specific for the analyte and forms a detectable complex with said analyte; and
   determining the presence or amount of said detectable complex as a measure of said analyte in said sample.

16. A test kit, comprising the reagent of claim 1.
17. A test kit, comprising the reagent of claim 4.
18. A test kit, comprising the reagent of claim 9.

* * * * *